(12) United States Patent
Ganguli et al.

(10) Patent No.: US 10,151,684 B2
(45) Date of Patent: Dec. 11, 2018

(54) HANDLE TRIBOMETER

(71) Applicant: DUCOM INSTRUMENTS (PVT) LTD, Bangalore (IN)

(72) Inventors: Amit Ganguli, Bangalore (IN); Narendra Mohan Dube, Bangalore (IN)

(73) Assignee: DUCOM INSTRUMENTS (PVT) LTD, Bangalore (IN)

(*) Notice: Subject to any disclaimer, the term of this patent is extended or adjusted under 35 U.S.C. 154(b) by 2 days.

(21) Appl. No.: 15/300,261

(22) PCT Filed: Mar. 30, 2015

(86) PCT No.: PCT/IN2015/000154
§ 371 (c)(1),
(2) Date: Sep. 28, 2016

(87) PCT Pub. No.: WO2015/145466
PCT Pub. Date: Oct. 1, 2015

(65) Prior Publication Data
US 2017/0138839 A1    May 18, 2017

(30) Foreign Application Priority Data
Mar. 28, 2014  (IN) .......................... 1674/CHE/2014

(51) Int. Cl.
*G01N 19/02*    (2006.01)
*G01L 1/22*    (2006.01)
(52) U.S. Cl.
CPC ............... *G01N 19/02* (2013.01); *G01L 1/22* (2013.01)

(58) Field of Classification Search
CPC .............................. G01C 19/02; G06F 3/016
USPC ................................................................ 73/9
See application file for complete search history.

(56) References Cited

U.S. PATENT DOCUMENTS

| 6,122,538 | A | 9/2000 | Sliwa | |
|---|---|---|---|---|
| 6,309,363 | B1* | 10/2001 | Chen | A61B 5/0057 600/587 |
| 7,958,775 | B2 | 6/2011 | Zahouani | |
| 8,695,398 | B2 | 4/2014 | Johnson | |

(Continued)

OTHER PUBLICATIONS

Thomas, Shane, "International Search Report," International Application No. PCT/IN2015/000154, dated Oct. 15, 2015, 3 pages.

*Primary Examiner* — Son Le
*Assistant Examiner* — Tarun Sinha
(74) *Attorney, Agent, or Firm* — Mannava & Kang, P.C.; Vinay Malik

(57) ABSTRACT

An apparatus 100 to estimate co-efficient of friction between a first sample member 103 and a second sample member 105 includes a housing 101, a measuring tip 104 extending from the housing 101. Further, the apparatus includes a multi-axis load sensor 107 disposed inside the housing 101 to measure components of load acting on the measuring tip 104. Further, the apparatus includes a motion and orientation measurement sensor 109 connected to the measuring tip 104 to measure components of acceleration and orientation of the measuring tip 104 with respect to a reference frame. Furthermore, the apparatus includes an output unit 111 to acquire, and process values from the multi-axis load sensor 107 and the motion and orientation measurement sensor 109 to estimate the co-efficient of friction.

14 Claims, 3 Drawing Sheets

(56) References Cited

U.S. PATENT DOCUMENTS

| | | | |
|---|---|---|---|
| 2009/0031791 A1* | 2/2009 | Zahouani | A61B 5/441 73/105 |
| 2012/0240660 A1* | 9/2012 | Johnson | G01N 19/02 73/9 |

* cited by examiner

HANDLE TRIBOMETER

CROSS REFERENCES TO RELATED APPLICATION

The present application is a national phase application of international application number PCT/IN2015/000154, filed on 30 Mar. 2015 which claims priority from, Indian Application Number 1674/CHE/2014, filed on 28 Mar. 2014, the disclosure of which is hereby incorporated by reference herein.

TECHNICAL FIELD

The embodiments herein relate to an apparatus and a method to derive co-efficient of friction (COF) between two sample materials. More specifically, to evaluate frictional and normal loads at an interface between a first sample member and a second sample member, and to estimate co-efficient of friction between the first sample member and the second sample member.

BACKGROUND

There are currently different techniques for characterizing mechanical, tribological, physiochemical or other properties of metals, non-metals, chemicals, materials, surfaces, and lubricants, which use controlled mechanical action on the surface of object to characterize a property of the surface. In these techniques, a handheld tool or tool held by some mechanical means exerts a force on the surface to be characterized which is usually normal to the surface. Also, in some cases when motion is imparted to the hand-held tool or tool held by some mechanical means on the surface to be characterized a friction force is always produced in the direction opposite to the direction of motion. The measurement of the frictional force and the applied load with high precision and reproducibility are conditions necessary for many characterization techniques. Further, to characterize different objects and materials such as ceramics, metals, metal alloys, polymers, composite materials, non-metals, physical objects, regions of animal and human body, hard surface coatings, solid and liquid lubricants, etc., which have very different mechanical properties the device needs to have a broad range of measuring capacity.

Characterization of surface properties of regions of human body or animal body, plays an important role as many consumer products are applied to the skin, hair, teeth and other regions of body. Consumer preferences are influenced by various factors, including product effectiveness, the feel of the product, fragrance, durability, ease of rinsing, etc. One way to determine consumer preferences is by conducting consumer marketing tests, in which a representative group of consumers provide feedback after using a product. Consumer marketing tests have several drawbacks, because consumers must be appropriately selected and compensated for their time, hence such tests are expensive and time consuming. Also, human feedback is inherently subjective, and may raise concerns about reliability, and the analyses, that can be performed after application, are limited.

There are several methods and devices for characterizing surface properties of regions such as skin, teeth, hair etc., One of which is use of a flexible member with a well determined stiffness constant. This flexible member is usually located between an attachment and the hand-held tool which exerts force on the sample. The normal force exerted by the hand-held tool on a surface is determined by the deflection of the flexible member in the direction normal to the surface of the sample. The frictional force resulting from the friction between the hand-held tool and the surface to be characterized is determined by the deflection of the flexible member in the direction opposed to the direction of motion.

In conventional devices the deflection of the flexible member is measured by means of a sensor, which by way of illustration can be one of the following types: fiber optic, capacitive, inductive, laser interferometric sensor, strain gauge or the like. One of the most widely used ones is the strain gauge. Another known conventional device for evaluation of frictional and normal loads between a two surfaces or objects comprises a measuring arm having a measuring sensor capable of measuring a frictional force being exerted on a tip. The devices described above measures either one of the frictional force or the stiffness constant, but does not provide a means to determine the motion of the hand held device and to estimate the co-efficient of friction between the surfaces to be characterized. Further, these devices are used only for a very narrow and well defined range of parameters, orientation and motion. Also, these device are generally used only under defined or controlled conditions. Thus, the modes of operation and evaluation of these devices are limited. Furthermore, the conventional devices requires a skilled operator to handle the device under controlled laboratory conditions.

Thus there exists a need for an apparatus to estimate the co-efficient of friction between two surfaces or members, without the need for a skilled operator. Further, there exists a need for an apparatus that can perform evaluations for a wide range of parameters, orientation and motion. Furthermore, there also exists another need to estimate the operating conditions during the evaluations. In addition, there exists yet another need to carry out these evaluations without controlled conditions. Additionally, there exists a need for an apparatus that can overcome the aforementioned drawbacks. The principle object of the embodiments herein is to provide an apparatus to estimate co-efficient of friction between a first sample member and a second sample member.

OBJECTS

The principle object of the embodiments herein is to provide an apparatus to estimate co-efficient of friction between a first sample member and a second sample member.

Another object of the embodiments herein is to evaluate frictional and normal loads at an interface between a first sample member and a second sample member.

Yet another object of the embodiments herein is to provide an apparatus to define, acquire, and process at least one of resultant load, friction force in a direction opposite to direction of motion of the first sample member, normal load in a direction orthogonal to direction of motion in the plane where vectors of direction of motion and resultant load lie, translatory and rotational acceleration of the first sample member, gravitational loads of the first sample member, and orientation of the first sample member.

Still another object of the embodiments herein is to provide an apparatus having at least one of multi-axis accelerometer, multi-axis gyroscope, multi-axis inclinometer, and multi-axis magnetometer to estimate direction of motion of a first sample member with respect to a reference frame.

Another object of the embodiments herein is to provide a method to estimate co-efficient of friction between a first sample member and a second sample member.

These and other objects of the embodiments herein shall be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

SUMMARY

Accordingly an apparatus to estimate co-efficient of friction between a first sample member and a second sample member is provided. The apparatus includes a housing, and a measuring tip extending from the housing. Further, the apparatus includes a multi-axis load sensor disposed inside the housing to measure components of load acting on the measuring tip. Further, the apparatus includes a motion and orientation measurement sensor connected to the measuring tip to measure components of acceleration and orientation of the measuring tip with respect to a reference frame. Furthermore, the apparatus includes an output unit to acquire, and process values from the multi-axis load sensor and the motion and orientation measurement sensor to estimate the co-efficient of friction.

A method to estimate co-efficient of friction between a tribo-pair having a first sample member and a second sample member is explained herein below. The method includes providing a housing, and a measuring tip extending from the housing. The housing includes a hollow interior region. Further, the method includes providing at least one multi-axis load sensor inside the housing to measure components of load acting on the measuring tip. Furthermore, the method includes providing at least one motion and orientation measurement sensor to measure components of acceleration and orientation of the measuring tip with respect to a reference frame. In addition, the method includes measuring and acquiring values from the multi-axis load sensor and the motion and orientation measurement sensor using an output unit to estimate co-efficient of friction.

BRIEF DESCRIPTION OF DRAWINGS

An exemplary embodiment is illustrated in the accompanying drawings, throughout which like reference letters indicate corresponding parts in the various figures. The exemplary embodiments herein will be better understood from the following description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. For example, although, some embodiments herein are explained with respect to an apparatus 100 to estimate co-efficient of friction at an interface of a tribo-pair for the ease of describing, it should be noted that the apparatus 100 could be used for measuring and determining any other desired parameters by incorporating the subject matter with little or no modifications. Accordingly, the examples should not be construed as limiting the scope of the embodiments herein.

Figure 1A:
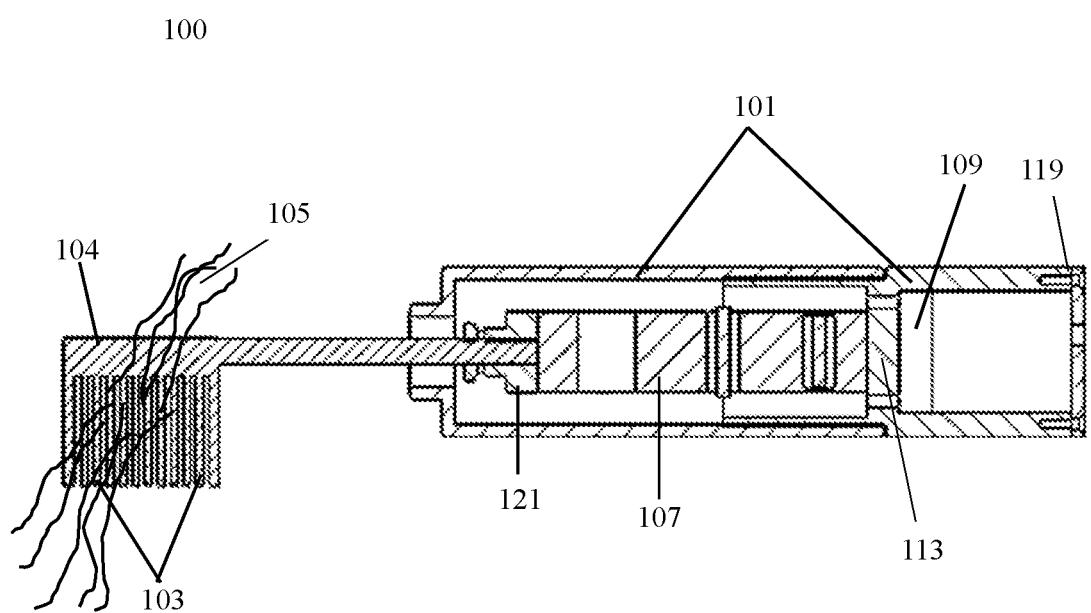
FIG. 1A illustrates a sectional view of an apparatus 100 according to an embodiment as disclosed herein.

The embodiments herein achieve an apparatus 100 to measure frictional and normal loads at the interface of a tribo-pair having a first sample member and a second sample member, and to estimate co-efficient of friction between the first sample member and the second sample member. Further, the embodiments herein achieve the apparatus 100 having at least one of multi-axis accelerometer, multi-axis gyroscope, multi-axis inclinometer, and multi-axis magnetometer to estimate the direction of motion of the first sample member with respect to a reference frame. Furthermore, the embodiments herein achieve the apparatus 100 having a data acquisition and processing system configured to define, acquire and process, at least one of output of a plurality of sensors to determine at least one of resultant load, friction force in a direction opposite to direction of motion of the first sample member, normal load in the direction orthogonal to the direction of motion in the plane where vectors of direction of motion and resultant load lie, translatory and rotational acceleration of the first sample member, gravitational loads of the first sample member, and orientation of the first sample member. Referring now to the drawings, and more particularly to FIGS. 1A through 2, where similar reference characters denote corresponding features consistently throughout the figures, there are shown embodiments.

Figure 1B:
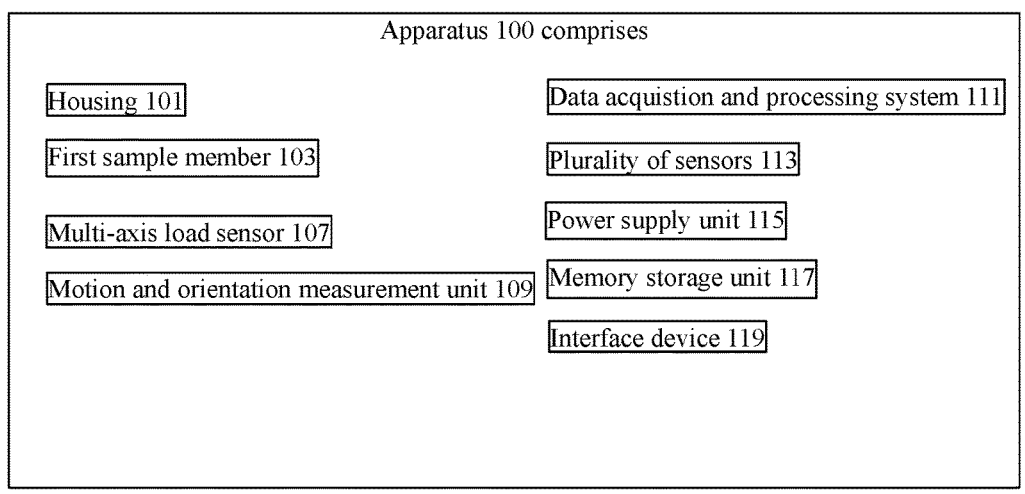
FIG. 1B illustrates components of the apparatus 100 according to an exemplary embodiment as disclosed herein.
Figure 2:
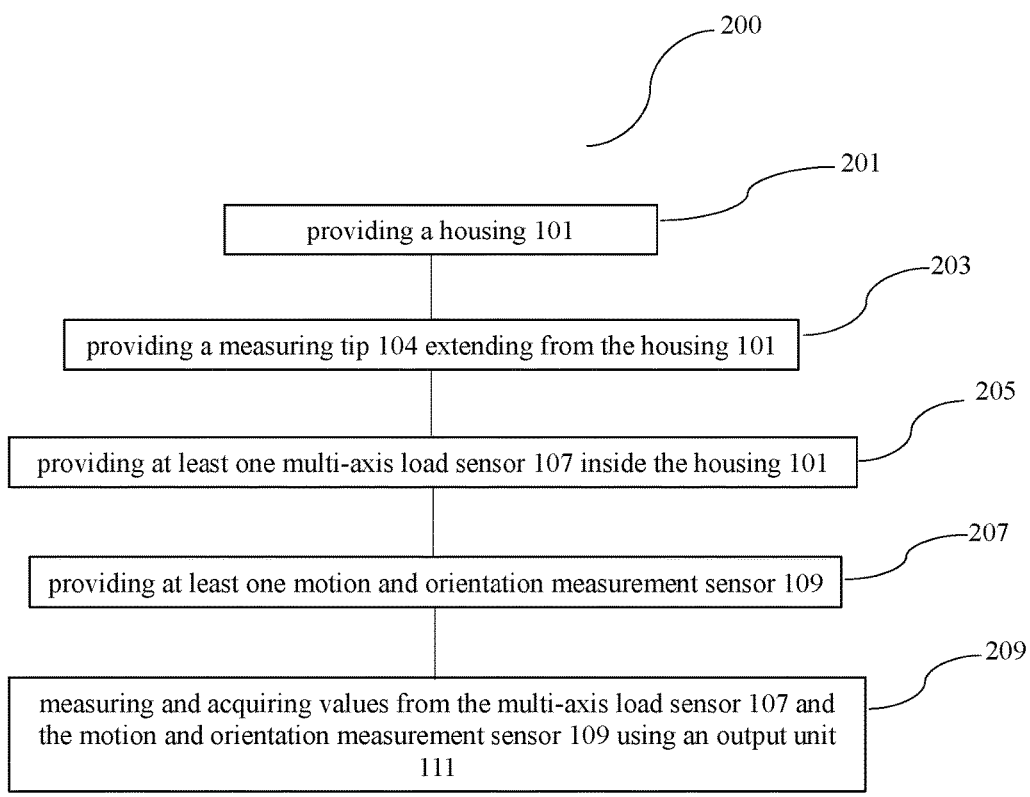
FIG. 2 depicts a method for estimating co-efficient of friction, according to an embodiment as disclosed herein.

Referring now to FIGS. 1A and 1B, the apparatus 100 includes a housing 101, a first sample member 103 (not shown in Figs), a measuring tip 104, a second sample member 105 (not shown in Figs), a multi-axis load sensor 107, a motion and orientation measurement sensor 109, an output unit 111, plurality of sensors 113, a power supply unit 115, a memory storage unit 117, an interface device 119, an attachment member 121, a multi-axis accelerometer 123, a multi-axis gyroscope 125, a multi-axis inclinometer 127, and a multi-axis magnetometer 129.

In one embodiment, the apparatus 100 includes the housing 101 which is made of predetermined shape, size and material. The housing 101 defines a plurality of hollow interior region to receive the multi-axis load sensor 107, the motion and orientation measurement sensor 109, the plurality of sensors 113, and the attachment member 121. The top portion of the housing 101 is provided with an opening to connect the measuring tip 104 with the multi-axis load sensor 107 through the attachment member 121. In one embodiment, the housing 101 is mounted on a base station (not shown in Figs). The base station defines a reference position for the apparatus 100. In one exemplary embodiment, the housing 101 of the apparatus 100 is manufactured as a handle which could be gripped in hand of a user. Further, the housing 101 is fabricated in such a way that it includes one or more chambers which can be attached or detached based on components required for conducting a specific test.

It should be noted that the aforemetioned configuration of the housing 101 is provided for ease of understanding of the embodiment. However, certain other embodiments may have a different configuration of the housing 101 and certain other embodiments which are also within the scope of the embodiment as disclosed may include or exclude certain components of the housing 101 and without otherwise deterring the intended function of the housing 101 as is apparent from this description and drawings.

In an embodiment, the apparatus 100 includes a plurality of sensors 113 to measure the conditions of the tribo-pair and the atmosphere during evaluation. The plurality of sensors 113 are selected from a group consisting of temperature sensors, humidity sensors, pressure sensor, resistivity sensors, capacitive sensors, moisture sensor, an image sensor, a microphone, a global positioning system, a local positioning system, and a time recorder. In an exemplary embodiment, the sensors 113 can be a single sensor, or can be a combination of two or more sensors.

It should be noted that the aforemetioned description of plurality of sensors 113 is provided for ease of understanding of the embodiment. However, certain other embodiments which are also within the scope of the embodiment as disclosed may have a different combinations of the sensors 113 and certain other embodiments may include or exclude certain sensors 113 and without otherwise deterring the intended function of the plurality of sensors 113 as is apparent from this description and drawings.

In an embodiment, the apparatus 100 includes the multi-axis load sensor 107 which is configured to measure the forces in three directions viz. x, y and z axes and moments along these three axes. Through the attachment member 121, the force being exerted on the measuring tip 104 is sensed which deforms a strain gauge. The strain gauge measures the deformation as a change in electrical resistance, which is a measure of the strain and hence the applied forces or loads. In one exemplary embodiment, the multi-axis load sensor 107 consists of twenty four strain gauges which are arranged in six full Wheatstone bridges having four strain gauges in each wheatstone bridge configuration. The wheatstone bridge is well suited for measurement of small changes of a resistance and is, therefore suitable for measuring the resistance change in the strain gauge. The output obtained from the strain gauge is in the order of a few microvolts and hence the apparatus 100 is supplied with an amplifier (not shown) to amplify the voltage readings.

In an embodiment, the measuring tip 104 is made up of the first sample member 103. The first sample member 103 is selected from a group comprising of a comb, a hair brush, a hair roller, a spiked brush, a tooth brush, a sponge, a loofah, a flat plate with emery, a razor, a plate with artificial skin, an artificial finger, a nail file, a cosmetic applicator, a scratcher, a writing instrument, a fixed ball, a rolling ball, a fixed cylinder, a rolling cylinder, an indentor, an ear-bud, a hand tool, a power tool, a cutting equipment, a sport equipment, a hand held device, a sample of any material mounted on a flat plate, and a sample of any material mounted on a curved plate. In one embodiment, the first sample member 103 is connected to the multi-axis load sensor 107 through the attachment member 121. The force exerted by the second sample member 105 on the first sample member 103 is measured using the multi-axis load sensor 107.

It should be noted that the aforemetioned first sample member 103 is provided for ease of understanding of the embodiment. However, certain other embodiments which are also within the scope of the embodiment as disclosed may have a different configurations of the first sample member 103 and certain other embodiments may include or exclude certain type of the first sample member 103 and without otherwise deterring the intended function of the first sample member 103 as is apparent from this description and drawings.

In an embodiment, the measuring tip 104 is provided with an unique identity code embedded in its body which is identified by the attachment member 121 to recognize the type of measuring tip 104. The recognized measuring tip 104 is configured to move in at least one of sliding, and rolling motion on the second sample member 105. In one embodiment, the second sample member 105 is selected from a group consisting of hair, teeth, fiber, skin, nail, a writing surface, a fixed ball, a rolling ball, a cylindrical roller for rolling contact, a sample of any material mounted on a flat surface, and a sample of any material mounted on a curved surface.

It should be noted that the aforemetioned second sample member 105 is provided for ease of understanding of the embodiment. However, certain other embodiments which are also within the scope of the embodiment as disclosed may have a different configurations of the second sample member 105 and certain other embodiments may include or exclude certain type of the second sample member 105 and without otherwise deterring the intended function of the second sample member 105 as is apparent from this description and drawings.

In an embodiment, the apparatus 100 includes the motion and orientation measurement sensor 109. The motion and orientation measurement sensor 109 detects the direction and motion of the measuring tip 104 which is acquired using the at least one of multi-axis accelerometer 123, multi-axis gyroscope 125, multi-axis inclinometer 127, and multi-axis magnetometer 129 with respect to a reference frame. The multi-axis accelerometer 123 measures the magnitude and direction of the proper acceleration (or g-force), as a vector quantity, and is used to sense orientation g-force of the measuring tip 104. The multi-axis gyroscope 125 measures the orientation of the measuring tip 104, based on the principles of angular momentum. The multi-axis inclinometer 127 measures the angular tilt of the measuring tip 104 with respect to a reference position. The multi-axis magnetometer 129 measures direction of the magnetic field at a point in the plane where vectors of direction of motion and resultant load lie. The measured values from the motion and orientation measurement sensor 109 are evaluated in the output unit 111 to determine the components of acceleration and orientation of the measuring tip 104 with respect to the reference frame.

It should be noted that the aforemetioned motion and orientation measurement sensor 109 is provided for ease of understanding of the embodiment. However, certain other embodiments which are also within the scope of the embodiment as disclosed may have a different configurations of the motion and orientation measurement sensor 109 and certain other embodiments may include or exclude certain type of the motion and orientation measurement sensor 109 and without otherwise deterring the intended function of the motion and orientation measurement sensor 109 as is apparent from this description and drawings.

In an embodiment, the apparatus 100 includes the output unit 111. The output unit 111 is configured to determine resultant loads from measured values of the multi-axis load sensor 107, and direction of motion of measuring tip 104 from measured values of the motion and orientation measurement sensor 109. The measured values are evaluated by the output unit 111 in order to transform the components of load in a direction opposite to the direction of motion to estimate the frictional load, and in a direction orthogonal to the direction of motion in the plane where vectors of direction of motion and resultant load lie to estimate the normal load. Further, the output unit 111 is interfaced with the interface device 119 to acquire, process and regulate the functioning of the apparatus 100. The interface device 119 includes power on-off switch/button, a device to display output of at least one of the plurality of sensors 113, the multi-axis load sensor 107, the motion and orientation measurement unit 109, and the output unit 111.

It should be noted that the aforemetioned interface device 119 is provided for ease of understanding of the embodiment. However, certain other embodiments which are also within the scope of the embodiment as disclosed may have a different configurations of the interface device 119 and certain other embodiments may include or exclude certain type of the interface device 119 and without otherwise deterring the intended function of the interface device 119 as is apparent from this description and drawings.

In an embodiment, the apparatus 100 further includes the power supply unit 115 and a memory storage unit 117. In one embodiment, the power supply unit 115 includes a battery charging element provided in the housing 101. The battery charging element is charged by at least one of electrical power supply, and a battery. A hole is provided at the bottom of the housing 101 to connect the power supply unit 115 to a charger. In one embodiment, the memory storage unit 117 is configured to store the measured values generated from at least one of the multi-axis load sensor 107, the motion and orientation measurement sensor 109, and the output unit 111. The memory storage unit 117 may be either provided in the housing 101 or may be integrated with the output unit 111.

It should be noted that the aforemetioned configuration of the apparatus 100 is provided for ease of understanding of the embodiment. However, certain other embodiments which are also within the scope of the embodiment as disclosed may have a different configurations of the apparatus 100 and certain other embodiments may include or exclude certain components of the apparatus 100 and without otherwise deterring the intended function of the apparatus 100 as is apparent from this description and drawings.

A method 200 to estimate co-efficient of friction between a tribo-pair having a first sample member 103 and a second sample member 105 is explained herein below. As shown in FIG. 2, the method 200 includes providing a housing 101 (step 201) and a measuring tip 104 extending from the housing 101 (step 203). The housing 101 includes a hollow interior region. Further, the method 200 includes providing at least one multi-axis load sensor 107 inside the housing 101 to measure components of load acting on the measuring tip 104 (step 205). Furthermore, the method includes providing at least one motion and orientation measurement sensor 109 to measure components of acceleration and orientation of the measuring tip 104 with respect to a reference frame (step 207). In addition, the method 200 includes measuring and acquiring values from the multi-axis load sensor 107 and the motion and orientation measurement sensor 109 using an output unit 111 (step 209) to estimate co-efficient of friction.

It should be noted that the aforementioned steps to estimate co-efficient of friction between a tribo-pair is provided for the ease of understanding of the embodiment. However, various steps provided in the above method may be performed in the order presented, in a different order, or simultaneously. Further, in some embodiments, one or more steps listed in the above method may be omitted. Therefore, such embodiments and any modification that is apparent from this description and drawings.

Procedure for Operating the Apparatus

The apparatus 100 initiates its operation as soon as it is picked up by the user. Once the apparatus 100 is picked in hand by the user, the apparatus 100 prompts the user to record the type of attachment that the user has selected for measuring the properties of the intended physical object. In this exemplary embodiment, measuring tip 104 is a comb and the intended physical object is hair. The apparatus 100 uses the interface device 119 to record this information of comb and hair. The apparatus 100 then prompts the user to start using the comb in its intended manner of use through the interface device 119. The intended manner of use herein is combing hair with the comb. During the usage of the comb the apparatus 100 records all the signals generated by a plurality of sensors 113 provided on tines of the comb. Further, images are captured using the interface device 119. The images are captured at different magnifications. The apparatus 100 uses a software embedded in the output unit 111 to sense that the user has stopped combing and facilitates the user to record the user's subjective observations of the experience.

All the inputs of the user, and the plurality of sensors 113 are stored in the memory storage unit 117. This data is accessed by the user or the tester or both at any time through the output unit 111. A specially developed software running either embedded on the memory storage unit 117 or on the output unit 111 is used to combine the data from the plurality of sensors, the multi-axis load sensor 107, and the motion and orientation measurement sensor 109 to evaluate the frictional force between the comb and hair, and to evaluate the direction, and orientation of comb 104 with respect to the direction of operation of the comb 104. Using these measured values the co-efficient of friction between the comb and hair is estimated.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

We claim:

1. An apparatus to evaluate in-situ frictional loads and normal loads between a tribo-pair, said tribo-pair having a first sample member, and a second sample member, said apparatus comprising:

a housing defining a hollow interior region therein;

a measuring tip extending from the housing;

at least one multi-axis load sensor disposed inside the housing and provided in communication with the measuring tip, wherein the multi-axis load sensor is configured to measure all components of loads acting on the measuring tip;

at least one motion and orientation measurement sensor provided in communication with the measuring tip, wherein the motion and orientation measurement sensor is configured to measure components of acceleration and orientation of the measuring tip in three mutually orthogonal directions with respect to a reference frame; and an output unit provided in communication with the multi-axis load sensor and the motion and orientation measurement sensor through an interface device, wherein the output unit is further configured to determine the frictional load by:

determining a resultant load vector using values measured by the multi axis load sensor;

determining a velocity vector based on the output of the motion and orientation measurement sensor;

determining a resultant plane using the resultant load vector and the velocity vector; and estimating the frictional load by transforming the components of resultant load in a direction opposite to the velocity vector in the resultant plane; and the output unit is further configured for determining the normal load by:

determining resultant load from measured values of the multi-axis load sensor;

determining direction of motion of measuring tip from measured values of the motion and orientation measurement sensor; and estimating the normal load by transforming the components of resultant load in a direction orthogonal to the direction of motion in the resultant.

2. The apparatus as claimed in claim 1, wherein the measuring tip is made up of first sample member and configured to move in at least one of sliding, and rolling motion on the second sample member.

3. The apparatus as claimed in claim 1, wherein the motion and orientation measurement sensor comprises at least one of multi-axis accelerometer, multi-axis gyroscope, multi-axis inclinometer, and multi-axis magnetometer.

4. The apparatus as claimed in claim 1, wherein the first sample member is selected from a group consisting of a comb, a hair brush, a hair roller, a spiked brush, a tooth brush, a sponge, a loofah, a flat plate with emery, a razor, a plate with artificial skin, an artificial finger, a nail file, a cosmetic applicator, a scratcher, a writing instrument, a fixed ball, a rolling ball, a fixed cylinder, a rolling cylinder, an indentor, an ear-bud, a hand tool, a power tool, a cutting equipment, a sports equipment, a hand held device, a sample of any material mounted on a flat plate, and a sample of any material mounted on a curved plate.

5. The apparatus as claimed in claim 1, wherein the second sample member is selected from a group consisting of hair, teeth, fibre, nail, a writing surface, a fixed ball, a rolling ball, a cylindrical roller for rolling contact, a sample of any material mounted on a flat surface, and a sample of any material mounted on a curved surface.

6. The apparatus as claimed in claim 1, wherein the housing encloses a plurality of sensors configured to measure the conditions of the tribo-pair and the atmosphere during evaluation selected from a group consisting of temperature sensors, humidity sensors, pressure sensor, resistivity sensors, capacitive sensors, moisture sensor, an image sensor, a global positioning system, local positioning system, and a time recorder.

7. The apparatus as claimed in claim 1, further comprises:

a power supply unit, wherein the power supply unit includes at least one of electrical power supply, battery, and battery charging element; and a memory storage unit, wherein the memory storage unit is configured to store the measured values of the multi-axis load sensor, the motion and orientation measurement sensor, the plurality of sensors, and the output unit.

8. The apparatus as claimed in claim 1, wherein said output unit is configured to communicate with the plurality of sensors, the multi-axis load sensor, the motion and orientation measurement sensor and the interface devices through wireless connection.

9. A method to evaluate in-situ frictional load and normal loads between a tribo-pair, said tribo-pair having a first sample member, and a second sample member, said method comprising:

providing a housing, said housing defining a hollow interior region;

providing a measuring tip extending from the housing, wherein the housing includes a hollow interior region;

providing at least one multi-axis load sensor inside the housing and in communication with the measuring tip to measure components of load acting on the measuring tip;

providing at least one motion and orientation measurement sensor to measure components of acceleration and orientation of the measuring tip in three mutually orthogonal directions with respect to a reference frame; and measuring and acquiring values from the multi-axis load sensor and the motion and orientation measurement sensor using an output unit, wherein the output unit if further configured to determine the frictional load by:

determining a resultant load vector using values measured by the multi axis load sensor;

determining a velocity vector based on the output of the motion and orientation measurement sensor;

determining a resultant plane using the resultant load vector and the velocity vector; and estimating the frictional load by transforming the components of resultant load in a direction opposite to the velocity vector in the resultant plane; and the output unit is further configured for determining the normal load by:

determining resultant loads from measured values of the multi-axis load sensor;

determining direction of motion of measuring tip from measured values of the motion and orientation measurement sensor; and estimating the normal load by transforming the components of resultant load in a direction orthogonal to the direction of motion in the resultant plane.

10. The method as claimed in claim 9, wherein the measuring tip is made up of first sample member which is configured to move in at least one of sliding, and rolling motion on the second sample member.

11. The method as claimed in claim 9, wherein the first sample member is selected from a group consisting of a comb, a hair brush, a hair roller, a spiked brush, a tooth brush, a sponge, a loofah, a flat plate with emery, a razor, a plate with artificial skin, an artificial finger, a nail file, a cosmetic applicator, a scratcher, a writing instrument, a fixed ball, a rolling ball, a fixed cylinder, a rolling cylinder, an indentor, an ear-bud, a hand tool, a power tool, a cutting equipment, a sports equipment, a hand held device, a sample of any material mounted on a flat plate, and a sample of any material mounted on a curved plate.

12. The method as claimed in claim 9, wherein the second sample member is selected from a group consisting of hair, teeth, fibre, nail, a writing surface, a fixed ball, a rolling ball, a cylindrical roller for rolling contact, a sample of any material mounted on a flat surface, and a sample of any material mounted on a curved surface.

13. The method as claimed in claim 9, wherein the motion and orientation measurement sensor comprises at least one of multi-axis accelerometer, multi-axis gyroscope, multi-axis inclinometer, and multi-axis magnetometer.

14. The method as claimed in claim 9, wherein the housing encloses plurality of sensors configured to measure the conditions of the tribo-pair and the atmosphere during evaluation selected from a group consisting of temperature sensors, humidity sensors, pressure sensor, resistivity sensors, capacitive sensors, moisture sensor, an image sensor, a global positioning system, local positioning system, and a time recorder.

* * * * *